United States Patent [19]

Cheng et al.

[11] Patent Number: 4,843,005
[45] Date of Patent: Jun. 27, 1989

[54] PROCESS FOR REGENERATING CORN

[75] Inventors: David S. K. Cheng, Foster City; Andrew S. Wang, Palo Alto, both of Calif.

[73] Assignee: Sungene Technologies Corporation, San Jose, Calif.

[21] Appl. No.: 897,209

[22] Filed: Aug. 18, 1986

[51] Int. Cl.$^4$ ............................................... C12N 5/00
[52] U.S. Cl. ........................... 435/240.49; 435/240.5; 435/240.51; 435/240.54
[58] Field of Search .............. 800/1; 435/240.1, 240.4, 435/240.45, 240.46–240.51; 47/58

[56] References Cited

U.S. PATENT DOCUMENTS

| | | | |
|---|---|---|---|
| 4,665,030 | 5/1987 | Close | 800/1 |
| 4,666,844 | 5/1987 | Cheng | 800/1 |

FOREIGN PATENT DOCUMENTS 0160390 6/1985 European Pat. Off. .

OTHER PUBLICATIONS

King et al. (1984), in Handbook of Plant Cell Culture, vol. 2, pp. 69–91.
C. E. Yeung et al., in *Plant Tissue Culture: Methods & Applications in Agriculture*, Thorpe, T. A., Ed., Academic Press, N.Y., pp. 252–271 (1981).
J. McD. Stewart, *Environmental and Experimental Botany*, 21, 301 (1981).
B. G. Gengenbach, *Crop Science*, 17, 489 (1977).
Y. P. S. Bajaj, *Journal of Experimental Biology*, 17, 475 (1979).
S. Dhaliwal et al., *Theor. Appl. Genet.*, 53, 43 (1978).
B. J. Reger et al., *Crop Science*, 22, 140 (1982).
K. R. Sarkar et al., *Indian Journal of Experimental Biology*, 18, 985 (1980).
B. G. Gengenbach, *Planta*, 134, 91 (1977).
K. Raman et al., *The Journal of Heredity*, 71, 311 (1980).
Y. P. S. Baja, *Cereal Research Communication*, 8, 359 (1980).
J. Straus, *American Journal of Botany*, 47, 640 (1960).
J. Straus et al., *American Journal of Botany*, 41, 687 (1954).
J. C. Shannon et al., *Crop Science*, 13, 491 (1973).
M. G. Neuffer et al., *Genetics*, 95, 929 (1980).
W. F. Sheridan et al., *The Journal of Heredity*, 73, 318 (1982).
W. F. Sheridan et al., *Genetics*, 95, 945 (1980).
N. Hrishi et al., citation unknown, published 1969.
K. Burghardtova et al., *Biologia Plantarium* (Praha), 22, 7 (1980).
E. G. Williams et al., *Bor. Gaz.*, 141, 252 (1980).
C. L. Armstrong et al., *Planta*, 164, 207 (1985).

*Primary Examiner*—Charles F. Warren
*Assistant Examiner*—David T. Fox
*Attorney, Agent, or Firm*—Robbins & Laramie

[57] ABSTRACT

The invention is directed to a process for regenerating plants from corn tissue. The process comprises the steps of in vitro conditioning of the corn tissue, culturing the corn tissue on a callus induction medium to induce callus, and regenerating plants from the callus. The callus may optionally be maintained prior to regeneration and the plants may optionally be cultured on an establishment medium prior to transfer to the soil.

20 Claims, No Drawings

PROCESS FOR REGENERATING CORN

BACKGROUND OF THE INVENTION

1. Field of the Invention

The present invention relates to a process for regenerating corn from tissue utilizing an in vitro conditioning step in the regeneration scheme.

2. Description of the Prior Art

Plant regeneration from cells in culture is essential for the application of somatic hybridization, for the production of new varieties through somaclonal variation and the use of genetic engineering in producing new varieties. Although plants can be regenerated from tissue culture of several varieties of corn, there are many varieties for which this has not been accomplished using similar techniques.

In recent years, plant cell culture successes have had a considerable influence on the understanding of the respective roles of cell and organism in control of plant growth and development. Isolated plant cells have been shown to be amenable to in vitro culture and complete plants have been regenerated from cultures derived from somatic tissues, either directly via somatic embryogenesis or indirectly via organogenesis. Generally the regeneration pathway of choice is determined empirically by the manipulation of extrinsic factors, especially growth regulators. Early investigations of certain plant species have suggested that exogenous auxin concentration is a major factor controlling somatic embryogenesis, such that its reduction leads to the initiation of embryoid formation. In other species, exposure to a definite balance of auxin and cytokinin leads to the occurrence of organogenesis (shoots, then roots).

The process which has become the standard system for corn tissue culture is described by Green et al., *Crop Science* 15, 417 (1975). In this process, immature embryos were plated onto a callus induction medium which comprises the MS mineral salts, Straus vitamins and amino acids (glycine, asparagine, niacin, thiamine, pyridoxine and pantothenic acid), 2% sucrose, 0.8% agar and a hormone selected from 2,4-dichlorophenoxyacetic acid (2,4-D), p-chlorophenoxyacetic acid (PCA), alpha-naphthaleneacetic acid (NAA), 2-isopentyladenine (2-ip) or mixtures thereof. Plantlets were regenerated by subculturing the callus on medium containing reduced hormone concentrations. Hormone concentrations which were useful were 3 mg/l 2,4-D and a mixture of 1 mg/l 2,4-D, 4 mg/l NAA and 0.05 mg/l 2-ip. Regeneration was then accomplished on medium containing 0.25 mg/l 2,4-D or a mixture of 1 mg/l NAA and 0.05 mg/l 2-ip, respectively. All culturing was conducted in a 16 hour light/8 hour dark cycle for 3-4 week intervals before transfer. This reference reports that callus induction did not occur in one of five genotypes tested.

Similar results with different media have been demonstrated by Freeling et al., *Maydica* 21, 97 (1976); Vasil et al., *Theor. Appl. Genet.* 66, 285 (1983); Edallo et al., *Maydica* 26, 39 (1981); LU et al., *Theor.Appl.Genet.* 62, 109 (1982); Hibberd et al., *Proc.Nat.Acad.Sci.USA* 74, 5113 (1977); and Green et al., *Crop Science* 14, 54 (1974). The latter reference also demonstrates genotype effects on callus induction.

Although this procedure has generally been unsuccessful for regenerating plants from all maize genotypes, the regeneration of most genotypes is now possible through the substitution of dicamba for 2,4-D in the media. See published European Application No. 0 177 738 and Ducan et al., *Planta* 165, 322 (1985).

None of the prior art demonstrates a conditioning step wherein the corn tissue is conditioned so that most genotypes can be regenerated from medium containing 284-D.

SUMMARY OF THE INVENTION

The present invention is directed to a process for regenerating plants from corn tissue. The process comprises the steps of in vitro conditioning of the corn tissue, culturing the corn tissue on a callus induction medium to induce callus, and regenerating plants from the callus. The callus may optionally be maintained prior to regeneration and the plants may optionally be cultured on an establishment medium prior to transfer to the soil.

Most genotypes of corn, including B73, can be regenerated using this procedure even when 2,4-D is utilized as a hormone in the callus induction medium.

DETAILED DESCRIPTION OF THE INVENTION

The present invention is directed to a process for regenerating corn, Zea mays, through the use of cell or tissue culture which includes a step of pre-conditioning the corn tissue prior to callus induction. In this process, regenerated plants are obtained which can be placed in soil and grown to maturation. In general, the process comprises: (a) in vitro conditioning of corn tissue, (b) culturing the pre-conditioned tissue on a medium to produce callus, and (c) regenerating plants from the callus. Prior to regeneration, the callus may also be cultured on a medium to maintain the callus for prolonged periods. The plants may also be cultured on a medium to establish them for transfer to soil.

It has been found that the in vitro conditioning step is necessary for the regeneration of plants from genotypes which have previously been recalcitrant to regeneration on medium containing 2,4-D. Such genotypes include B73, Mo17 and A632, among others. Any in vitro conditioning step may be utilized which conditions the corn tissue so that callus can be induced on medium containing 2,4-D. In one embodiment, in vitro fertilization is used as the in vitro conditioning step. In this embodiment, single ovules are fertilized by placing single or multiple pollen grains on silks which attach sectors/single ovules. The in vitro fertilized kernels are allowed to mature and the immature embryos removed after 10-17 days when they are about 1.0 mm to about 1.2 mm in length. The immature embroyos are then placed on a callus induction medium.

In a second embodiment, the in vitro conditioning is accomplished by isolating zygotes about 3 days post-pollination. The pericarp is removed from the zygote containing immature caroypsws. This material is then cultured on endosperm development medium for endosperm development and zygote maturation in the dark at 20°-30° C, preferably 30° C. When the immature embryo reaches the size of from about 1.0 mm to about 1.2 mm in length, it is isolated and cultured on the callus induction medium.

The endosperm development medium comprises mineral salts, vitamins, L-glutamine, and aucrose. The mineral salts comprise macroelements and microelements. The macroelements used in the induction medium may be the following compounds: magnesium sulfate, calcium chloride, monopotassium phosphate, potassium nitrate and ammonium nitrate. The microelements contained in this medium are: boric acid, manganese sulfate, zinc sulfate, sodium molybdate (VI), copper (II) sulfate, cobalt chloride, potassium iodide, iron (II) sulfate and disodium-ethylenediamine terraacetic acid (EDTA). This combination of mineral salts is known in the art as the MS mineral salts. Other combinations of mineral salts may also be used as long as they do not adversely affect endosperm development. Many combinations of mineral salts are known. These include, but are not limited to, N6, Heller, Nitsch and Nitsch, B5 and white.

The preferred amounts of the macroelements and microelements which are used to prepare one liter of medium are: 370 mg magnesium sulfate heptahydrate, 440 mg calcium chloride dihydrate, 170 mg monopotassium phosphate, 1900 mg potassium nitrate, 1650 mg ammonium nitrate, 6.2 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 27.8 mg iron (II) sulfate heptahydrate, and 37.3 mg disodium-EDTA.

The endosperm development medium further contains vitamins. The vitamins utilized are folic acid, nicotinic acid, thiamine, pyridoxine, glycine and biotin. This combination of vitamins is known in the art as Nitsch's vitamins. Other combinations of vitamins may be used as long as they do not affect endosperm development. The preferred amounts of vitamins which are used to prepare one liter of medium are: 0.50 mg folic acid, 5 mg nicotinic acid, 0.90 mg thiamine hydrochloride, 0.50 mg pyridoxine hydrochloride, 2 mg glycine and 0.05 mg biotin. This specific combination will be referred to herein as modified Nitsch's vitamins A.

The endosperm development medium contains 5-10%, preferably 7%, sucrose, 100-300 mg/l, preferably 200 mg/l, L-glutamine, and a gelling agent such as agar or Gelrite TM (Kelko Commercial Development, Post Office Box 23076, San Diego, California). It is preferred to use Gelrite at a concentration of 0.1%. The medium has a pH of 5.5-5.8 with a preferred pH of 5.8, and is sterilized by autoclaving.

In the third embodiment, zygotes are isolated from the embryo sac about 4 to 4.5 days post-pollination. The zygotes are cultured on a zygote maturation medium. The zygote would mature and could then be subjected to callus induction. The zygote maturation medium contains mineral salts, vitamins and sucrose. Them mineral salts are as described for the endosperm development medium.

The zygote maturation medium further contains vitamins. The vitamins utilized are myo-inositol and thiamine. The preferred amounts of the vitamins used to prepare one liter of medium are 0.4 mg thiamine hydrochloride and 100 mg myo-inositol.

The zygote maturation medium contains 1-3%, preferably 2%, sucrose, and a gelling agent such as agar or Gelrite. It is preferred to use Gelrite agent such as agar or Gelrite. It is preferred to use Gelrite at a concentration of 0.2%. The medium has a pH of 5.5-5.8, with a preferred pH of 5.8, and is sterilized by autoclaving.

In addition to the above components, the zygote maturation medium also contains a hormone. As used herein, "hormone" is intende to mean any natural or synthetic compound which has a regulatory effect on plants or plant tissues and any additive which may be combined with said compound. Plant hormones include auxins and cytokinins. Additives which may be included with auxins and cytokinins include coconut milk and casein hydrolysate.

It has been found that the hormone which is useful for zygote maturation is a mixture of 2,4-D and coconut milk. Generally, 0.7-1 mg/l 2,4-D and 5-15% coconut milk are present. It is preferred to utilize 1 mg/l 2,4-D and 10% coconut milk.

The zygote is plated on the zygote maturation medium and overlaid with, preferably, paraffin oil to prevent dehydration. The zygote is cultured in the dark at 25°-30° C., preferably 30° C.

Once the immature embryo has reached the appropriate size, from about 1.0 to about 1.2 mm, it is ready to be used for callus induction. Callus induction can occur by the continued culturing of the immature embryo on the zygote maturation medium. In this case, the immature embryo undergoes dedifferentiation and callus formation after about four weeks of culturing on the zygote maturation medium.

Alternatively, the immature embryo is cultured on a callus induction medium for the formation of callus, especially if the first or second embodiments for in vitro conditioning are utilized. The callus induction medium comprises mineral salts, vitamins, sucrose and a hormone. The mineral salts, vitamins and sucrose are the same as previously described for the zygote maturation medium. The callus induction medium is solidified using agar or Gelrite, preferably 0.2% Gelrite, as the gelling substance. The medium has a pH of 5.5-5.8, preferably 5.8, and is sterilized by autoclaving.

It has been found that the hormone which is useful for callus induction is a mixture of 2,4-D, NAA and alpha-indole butyric acid (IBA). Generally, 1-4 mg/l 2,4-D, 1-2 mg/l NAA and 1-2 mg/l IBA is used as the hormone. It is preferred to use 3 mg/l 2,4-D, 2 mg/l NAA and 2 mg/l IBA.

The immature embryo is plated on the callus induction medium and cultured in diffused light with a photoperiod of 16 hours at 20°-30° C. for about three to four weeks. During this time, the immature embryo undergoes dedifferentiation and callus formation.

After culturing on the callus induction medium, the callus is transferred and subcultured on a regeneration medium. The culturing on the regeneration medium is conducted as described for the callus induction medium for a period of two to three weeks. For the third induction medium for a period of two to three weeks. For the third embodiment, the zygote maturation medium also functions as the regeneration medium, as well as the callus induction medium, upon continued culturing of the callus on the zygote maturation medium. Plants form about two to three weeks after callus formation.

The regeneration medium comprises mineral salts, vitamins, sucrose and a hormone. These materials are the same as previously described for the zygote maturation medium. The medium is solidified using agar or Gelrite as previously described, and has a pH of 5.5-5.8, preferably 5.8.

The plants regenerated from the regeneration medium can be transferred directly to the soil and grown to maturation. Alternatively, the plants can first be cultured on an establishment medium. The establishment medium contains the same mineral salts and vitamins as the callus induction medium. It further contains sucrose in the same amount as the callud induction medium, i.e., 1-3%, preferably 2%. The establishment medium has a pH of 5.5-5.8, preferably 5.8, and is sterilized as described above. Gelrite, preferably 0.2%, or agar is used to solidify the medium.

After culturing the plantlets on the establishment medium for 7-21 days, preferably 10-15 days, in diffused light with a photoperiod of 16 hours per day, the plantlets are transferred to the soil. The plantlets are removed and the Gelrite is washed off. The plantlets are then planted in a mixture of one part potting soil and two parts Perlite. After three weeks, the plants are transplanted to a mixture of one part potting soil and one part Perlite.

In addition to culturing the callus on regeneration medium to produce plants, the callus may first be cultured to maintain it. If this approach, it utilized, the callus is transferred from the callus induction medium to a pre-maintenance medium and cultured in the dark at 24°-30° C., preferably 28° C., for about seven days.

The pre-maintenance medium comprises mineral salts, vitamins, sucrose and a hormone. The mineral salts, vitamins and sucrose are as described for the callus induction medium, except that 0.8 mg/l of thiamine hydrochloride is utilized. The hormone may be either 1-4 mg/l, preferably 2 mg/l, 2,4-D or 1-5 mg/l, preferably 2 mg/l dicamba. The pre-maintenance medium further contains amino acids, of which L-proline and casamino acids are utilized. 5-50 $\mu$M L-proline and 100-500 mg/l casamino acids are used. The preferred amounts are 10 mM L-proline and 100 mg/l casamine acids. The pre-maintenance medium is solidified using agar or Gelrite, preferably 0.2% Gelrite, as the gelling substance. The medium has a pH of 5.5-5.8, preferably 5.8, and is sterilized by autoclaving.

After culturing on the pre-maintenance medium, the callus is transferred and subcultured on a maintenance medium. It is important to select embryogenic, friable sectors of callus for transfer to the maintenance medium. This type of callus usually appears within 10-20 days of culture on the pre-maintenance medium. The callus is cultured on the maintenance medium as long as desired, with transfers to fresh medium occurring every 10-14 days. Callus has been maintained for more than 18 months. The culturing on the maintenance medium is performed in the dark at 24°-30° C., preferably 28° C.

The maintenance medium comprises mineral salts, vitamins, amino acids, sucrose and a hormone. The mineral salts and vitamins are the same as described for the callus induction medium, except that 0.8 mg/l of thiamine hydrochloride is utilized. This combination of vitamins will be referred to herein as modified Nitsch's vitamins B. 1-3%, preferably 2%, sucrose is utilized. The medium preferably contains Gelrite at about 0.2% and has a pH of 5.5-6.0, with 5.8 preferred. The maintenance medium also contains amino acids. The amino acids utilized are L-proline and casamino acids. 5-50 mM L-proline and 100-500 mg/l casamino acids are used. The preferred amounts are 10 mM L-proline and 100 mg/l casamino acids. Finally, the medium contains a hormone. 1-3 mg/l, preferably 2 mg/l, of 2,4-D is utilized. Alternatively, 1-4 mg/l, preferably 2 mg/l, dicamba or 1-4 mg/l, preferably 3 mg/l, chloramben are utilized.

After culturing the callus on the maintenance medium for the desired time period, the callus is transferred and subcultured on a regenration medium. The regeneration medium may be the regeneration medium as described above. Alternatively, the regeneration medium may also lack hormones, i.e., it does not contain any hormone. Culturing on the regeneration medium is performed at 24°-30° C., preferably 28° c., with a 16 hour diffused light/8 hour dark cycle. Plantlets are transferred to culture tubes containing fresh regeneration medium when they reach 1-3 cm in size for further development. When the plantlets reach 10-15 cm in size, they are transferred to soil and grown in the greenhouse.

Alternatively, the callus after maintenance is first transferred and subcultured on a pre-regeneration medium before transfer and subculture on the regeneration medium. Culturing on the pre-generation medium is performed for 10-20 days at 24°-30° C., preferably 28° C., with a 16 hour diffused light/8 hour dark cycle before transfer to the regeneration medium. The pre-generation medium comprises mineral salts, vitamins, amino acids, sucrose and a hormone. This medium is the same as the maintenance medium except that the concentration of the hormone is reduced. Generally, the hormone concentration is 0.05-0.5 $\mu$M, preferably 0.1 $\mu$M.

The process is useful for regenerating plants from the immature embryo of many cultivars of corn using 2,4-D. Other hormones can also be utilized in addition to 2,4-D as described herein. The present process is capable of regenerating cultivars of corn using medium with 2,4-D which were previously incapable of regeneration with 2,4-D-containing medium, according to prior art processes. Examples of these cultivars include B73, A632 and Mo17.

The present invention will be further described by reference to the following non-limiting examples. all of the cultivars of corn used herein are publicly available.

EXAMPLE 1

Preparation of Solutions

The following stock solutions or solutions were prepared for use in making the media described in further detail below.

1. Mineral Salts and Vitamins

The solution was prepared immediately before use by dissolving one packet of Murashige minimal organics medium without sucrose (Gibco Laboratories Catalog No. 510-3118) in 800 ml of distilled, deionized water. A small amount of the water was used to rinse out the packet. The packet includes a pH buffering agent.

2. Hormones (A) A 0.1 mg/ml stock solution of 2,4-D was prepared by dissolving 10 mg of 2,4-D in 10 ml of 70% ethanol and diluting to 100 ml with distilled, deionized water.

(B) A 0.1 mg/ml stock solution of IBA was prepared as described for 2,4-D.

(C) A 0.1 mg/l stock solution of NAA was prepared as described for 2,4-D.

(D) Coconut milk was prepared by decanting endosperm liquid from a coconut. The average volume of endosperm liquid is 100 ml. The liquid was heated to 90° C. for 3-5 minutes to precipitate protein and cooled to room temperature. The liquid was then filtered through Watman #3 filter paper and suction-filtered through a 47 mm Gelman glass fiber filter. The filtrate was stored frozen until used.

(E) 1 mg/ml stock solutions of 2,4-D dicamba or chloramben were prepared by dissolving 50 mg of the hormone in 50 ml of sterile, deionized water.

3. Nitsch's Vitamins

A 100X stock solution of Nitsch's vitamins was prepared by dissolving 5 mg of folic acid, 50 mg of nicotinic acid, 5 mg of pyridoxine hydrochloride, 5 mg of thiamine hydrochloride, 20 mg of glycine and 0.5 mg of biotin in 100 ml of distilled, deionized water.

EXAMPLE 2

Preparation of Media

1. Endosperm Development Medium

Endosperm development medium was prepared by adding 70 g of sucrose, 10 ml of the 100X stock solution of Nitsch's vitamins and 200 mg of L-glutamine to the mineral salts and vitamins solution. 1 g of Gelrite was added and the volume brought to one liter with distilled, deionized water. The medium was then sterilized by autoclabing and poured into petri dishes.

2. Zygote Maturation Medium

Zygote maturation medium was prepared by adding 20 g of sucrose, 10 ml of the 0.1 mg/ml 2,4-D stock solution and 100 of coconut milk to the mineral salts and vitamins solution. 2 g of Gelrite was added and the volume brought to one liter with distilled, deionized water. The medium was sterilized by autoclaving and poured into petri dishes.

3. Callus Induction Medium

Callus induction medium was prepared by adding 20 g of sucrose, 30 ml of the 0.1 mg/ml 2,4-D stock solution, 20 ml of NAA stock solution, and 20 ml of IBA stock solution to the mineral salts and vitamins solution. 2 g of Gelrite was added and the volume brought to one liter with distilled, deionized water. The medium was sterilized by autoclaving and poured into petri dishes.

4. Regeneration Medium A

Regeneration medium A was prepared as described for the zygote maturation medium.

5. Regeneration Medium B

Regeneration medium B was prepared as described for the zygote maturation medium, except that 2,4-D and coconut milk were not added.

6. Pre-Maintenance Medium

Pre-maintenance medium was prepared by dissolving one packet of Murashige minimal organics medium without sucrose which contains a pH buffering agent (Gibco Catalog No. 500-3118), 20 g of sucrose, 0.4 mg of thiamine hydrochloride, 100 mg casamine acids, 1.15 ml L-proline and 2 ml of the 1 mg/ml 2,4-D stock solution in 800 ml of sterile, deionized water. A small amount of water was used to rinse out the packet. 2 g of Gelrite was added and the volume brought to one liter with deionized water. The medium was sterilized by autoclaving and poured into petri dishes.

7. Maintenance Medium

Maintenance medium was prepared as described for pre-maintenance medium using the appropriate amount of hormone stock solution.

8. Pre-Regeneration Medium

Pre-generation medium was prepared as described for pre-maintenance medium using the appropriate amount of hormone stock solution.

9. Establishment Medium

Establishment medium was prepared as described for regeneration medium B.

EXAMPLE 3

Corn Regeneration

Single or multiple pollen grains were placed in vitro on silk attaching sectors/single ovules. Immature embryos were isolated from the in vitro fertilized B73 kernels when they were about 1.0–1.2 mm in length. The kernels were surface-sterilized in a 20% bleach solution for 20 minutes and rinsed twice in 500 ml of sterile water. The embryos were then removed from each kernel and plated onto callus induction medium with the embryo axis in contact with the medium. Culturing was conducted in a 16 hour diffused light/8 hour dark cycle at about 24° C. for four weeks. The callus was then transferred to regeneration medium A and cultured for two weeks in a 16 hour diffused light/8 hour dark cycle. Regenerated plants were matured by culturing on establishment medium for two weeks, and then transferred to soil and matured in a greenhouse.

EXAMPLE 4

Corn Regeneration

Three days post-pollinated, intact B73 zygotes were isolated and the pericarp removed with a syringe needle. The zygotes in the immature caryopses were plated at an angle onto the endosperm development medium. The endosperms enlarged and exposed the immature embryos suring culturing in the dark at 30° C. The embryos were isolated when they were about 1.0–1.2 mm in length and plated onto the callus induction medium with the embryo axis in contact with the medium. Culturing was conducted for four weeks in the light as described above. Plants were regenerated from the callus as described in Example 3, and grown to maturity in a greenhouse.

EXAMPLE 5

Corn Regeneration

Four days post-pollinated B73 zygotes were isolated and removed from the endosperm. The zygotes, which did not contain any other structures, were plated onto zygote maturation medium. Paraffin oil was overlaid on each zygote to prevent dehydration. After culturing for four weeks in the dark at 30° C., the immature embryo matured and formed callus. Plants were regenerated by continued culturing in the light, and were transferred to establishment medium and soil as described in Example 3. The regenerated plants were grown to maturity in a greenhouse.

EXAMPLE 6

Corn Regeneration

B73 callus was obtained as described in Example 3 and transferred to pre-maintenance medium containing 2 mg/l 2,4-D. The callus was cultured in the dark for one week at 27° C. The friable callus with embryogenic potential was visually selected and transferred to maintenance medium containing 2 mg/l 2,4-D. The callus was cultured in the dark at 27° C. with transfers made to fresh maintenance medium every 10–14 days. Several friable, embryogenic, fast-growing cell lines were isolated after three subcultures. The cell lines have been maintained for approximately one year without showing a decrease in their quality. For generation, the callus was transferred onto regeneration medium B and cultured in a 16 hour diffused light/8 hour dark cycle at 27° C. 10–30 days after transfer to regeneration medium B, 1–3 cm plants were transferred to culture tubes containing fresh regeneration medium B. When the plants were 10–15 cm in height, they were transferred to soil and matured in a greenhouse.

EXAMPLE 7

Four days post-pollinated A632 zygotes were isolated and plated on zygote maturation medium as described in Example 5 to mature the zygote and form callus. The callus was cultured in the dark at 28° C. for one week. The friable callus with embroygenic potential was visually selected and transferred to maintenance medium containing 2 mg/l 2,4-D, and handled as in Example 6 to regenerate plants.

EXAMPLE 8

Four days post-pollinated Mo17 zygotes were isolated and plated on zygote maturation medium as described in Example 5 to mature the zygote and form callus. The callus was cultured in the dark at 28° C. for 10–20 days. The friable callus with embryogenic potential was visually selected and transferred to maintenance medium containing 2 mg/l dicamba, and handled as in Example 6 to regenerate plants.

While the invention has been described in connection with specific embodiments thereof, it will be understood that it is capable of further modifications. This application is intended to cover any variations, uses or adaptation of the invention following in general, the principles of the invention and including such departures from the present disclosure as come within known and customary practice within the art to which the invention pertains.

What is claimed is:

1. A process for regenerating corn plants from 2,4-D recalcitrant genotypes through cell or tissue culture which comprises the steps of:
   (a) in vitro conditioning a zygote to obtain a conditioned immature embryo wherein said in vitro conditioning is performed by a method selected from the group consisting of:
     (1) in vitro fertilization;
     (2) isolating an intact zygote about three days post-pollination, removing the pericarp, and culturing the remaining material on an endosperm development medium which comprises mineral salts, vitamins, L-glutamine and sucrose; and
     (3) isolating an individual zygote from the embryo sack about four to four and one-half days post-pollination, and culturing the zygote on a zygote maturation medium which comprises mineral salts, vitamins, sucrose and a mixture of 2,4-D and coconut milk as a hormone;
   (b) culturing the conditioned immature embryo on a callud induction medium comprising mineral salts, vitamins, sucrose and a hormone selected from the group consisting of (1) a mixture of 2,4-dichlorophenoxyacetic acid (2,4-D), α-naphthalene acetic acid (NAA) and α-indole butyric acid (IBA), and (2) a mixture of 2,4-D and coconut milk for callus formation; and
   (c) subculturing said callus on a regeneration medium comprising mineral salts, vitamins and sucrose for plant formation.

2. The process of claim 1 wherein said regeneration medium further comprises a mixture of 2,4-D and coconut milk as a hormone.

3. The process of claim 2 which further comprises the step of:
   (d) subculturing the plants on an establishment medium which comprises mineral salts, vitamins and sucrose to establish the plants.

4. The process of claim 1 which further comprises the steps of:
   (b1) culturing said callus on a pre-maintenance medium which comprises mineral salts, vitamins, sucrose, L-proline, casamino acids and a hormone selected from the group consisting of 2,4-D and dicamba in the dark at 24°–30° C.; and
   (b2) culturing the resulting callus on a maintenance medium which comprises mineral salts, vitamins, sucrose, L-proline, casamino acids and a hormone selected from the group consisting of 2,4-D, dicambe and chloramben in the dark at 24°–30° C. for callus maintenance.

5. The process of claim 4 which further comprises the step of:
   (b3) culturing the maintained callus on a pre-regeneration medium which comprises mineral salts, vitamins, sucrose, L-proline, casamino acids and a hormone selected from the group consisting of 2,4-D, dicamba and chloramben in an amount of 0.05–0.5 $\mu M$ in thelight at 24°–30° C.

6. The process of claim 1 wherein the concentration of hormones in the callus induction medium is (1) 1–4 mg/l 2,4-D, 1–2 mg/l NAA and 1–2 mg/l IBA or (2) 0.7–1 mg/l 2,4-D and 5–15% coconut milk.

7. The process of claim 2 wherein the concentration of hormones is
   (i) (1) 1–4 mg/l 2,4-D, 1–2 mg/l NAA and 1–2 mg/l IBA or (2) 0.7–1 mg/l 2,4-D, and 5–15% coconut milk in the callus induction medium, and
   (ii) 0.7–1 mg/l 2,4-D and 5–15% coconut milk in the regeneration medium.

8. The process of claim 3 wherein the concentration of hormones is
   (i) (1) 1–4 mg/l 2,4-D, 1–2 mg/l NAA and 1–2 mg/l IBA or (2) 0.7–1 mg/l 2,4-D and 5–15% coconut milk in the callus induction medium, and
   (ii) 0.7–1 mg/l 2,4-D and 5–15% coconut milk in the regeneration medium.

9. The process of claim 4 wherein the concentration of hormones is
   (i) (1) 1–4 mg/l 2,4-D, 1–2 mg/l NAA and 1–2 mg/l IBA or (2) 0.7–1 mg/l 2,4-D and 5–15% coconut milk in the callus induction medium;
   (ii) (1) 1–4 mg/l 2,4-D or (2) 1–5 mg/l dicamba in the pre-maintenance medium; and
   (iii) (1) 1–3 mg/l 2,4-D, (2) 1–4 mg/l dicamba, or (3) 1–4 mg/l chloramben in the maintenance medium.

10. The process of claim 9 wherein the concentration of L-proline is 5–50 mM and the concentration of casamino acids is 100–500 mg/l.

11. The process of claim 5 wherein the concentration of hormones is
   (i) (1) 1–4 mg/l 2,4-D, 1–2 mg/l NAA and 1–2 mg/l IBA or (2) 0.7–1 mg/l 2,4-D and 5–15% coconut milk in the callus induction medium;
   (ii) (1) 1–4 mg/l 2,4-D or (2) 1–5 mg/l dicamba in the pre-maintenance medium;
   (iii) (1) 1–3 mg/l 2,4-D, (2) 1–4 mg/l dicamba or (3) 1–4 mg/l chloramben in the maintenance medium.

12. The process of claim 11 wherein the concentration of L-proline is 5–50 mM and the concentration of casamino acids is 100–500 mg/l.

13. The process of claim 6 wherein the glutamine concentration is 200 mg/l.

14. A process for regenerating corn plants from 2,4-D recalcitrant genotypes through cell or tissue culture which comprises the steps of:

(a) in vitro conditioning a zygote to obtain a conditioned immature embryo wherein said in vitro conditioning is performed by a method selected from the group consisting of:
   (1) in vitro fertilization;
   (2) isolating an intact zygote about three days post-pollination, removing the pericarp, and culturing the remaining material on an endosperm development medium which comprises mineral salts, vitamins, L-glutamine and sucrose; and
   (3) isolating an individual zygote from the embryo sack about four to four and one-half days post-pollination, and culturing the zygote on a zygote maturation medium which comprises mineral salts, vitamins, sucrose and a mixture of 2,4-D and coconut milk as a hormone;
(b) culturing the conditioned immature embryo on a callus induction medium comprising mineral salts, vitamins, sucrose and a hormone selected from the group consisting of (1) a mixture of 2,4-dichlorophenoxyacetic acid (2,4-D), α-naphthalene acetic acid (NAA) and α-indole butyric acid (IBA), and (2) a mixture of 2,4-D and coconut milk for callus formation;
(c) culturing said callus on a pre-maintenance medium which comprises mineral salts, vitamins, sucrose, L-proline, casamino acids and a hormone selected from the group consisting of 2,4-D and dicamba in the dark at 24°–30° C.;
(d) culturing the resulting callus on a maintenance medium which comprises mineral salts, vitamins, sucrose, L-proline, casamino acids and a hormone selected from the group consisting of 2,4-D, dicamba and chloramben in the dark at 24°–30° C. for callus maintenance; and
(e) subculturing said callus on a regeneration medium comprising mineral salts, vitamins and sucrose for plant formation.

15. The process of claim 14 which further comprises the step of:
   (d1) culturing the maintained callus on a pre-regeneration medium which comprises mineral salts, vitamins, sucrose, L-proline, casamino acids and a hormone selected from the group consisting of 2,4-D, dicamba and chloramben in an amount of 0.05–0.5 μM in the light at 24°–30° C.

16. The process of claim 14 wherein the concentration of hormones
   (i) (1) 1–4 mg/l 2,4-D, 1–2 mg/l NAA and 1–2 mg/l IBA or (2) 0.7–1 mg/l 2,4-D and 5–15% coconut milk in the callus induction medium;
   (ii) (1) 1–4 mg/l 2,4-D or (2) 1–5 mg/l dicamba in the pre-maintainance medium; and
   (iii) (1) 1–3 mg/l 2,4-D, (2) 1–4 mg/l dicamba, or (3) 1–4 mg/l chloramben in the maintenance medium.

17. The process of claim 16 wherein the concentration of L-proline is 5–50 mM and the concentration of casamino acids is 100–500 mg/l.

18. The process of claim 15 wherein the concentration of hormones is
   (i) (1) 1–4 mg/l 2,4-D, 1–2 mg/l NAA and 1–2 mg/l IBA or (2) 0.7–1 mg/l 2,4-D and 5–15% coconut milk in the callus induction medium;
   (ii) (1) 1–4 mg/l 2,4-D, (2) 1–5 mg/l dicamba in the pre-maintenance medium; and
   (iii) (1) 1–3 mg/l 2,4-D, (2) 1–4 mg/l dicamba or (3) 1–4 mg/l chloramben in the maintenance medium.

19. The process of claim 18 wherein the concentration of L-proline is 5–50 mM and the concentration of casamino acids is 100–500 mg/l.

20. The process of claim 16 wherein the glutamine concentration is 200 mg/l.

* * * * *